United States Patent [19]

Das et al.

[11] Patent Number: 4,767,756
[45] Date of Patent: Aug. 30, 1988

[54] 3-SUBSTITUTED BENZAZEPINES

[75] Inventors: Jagabandhu Das, Hamilton Square; David M. Floyd, Pennington, both of N.J.

[73] Assignee: E. R. Squibb & Sons, Inc., Princeton, N.J.

[21] Appl. No.: 74,734

[22] Filed: Jul. 17, 1987

[51] Int. Cl.$^4$ .................. A61K 31/55; C07D 401/04; C07D 401/06; C07D 401/14; C07D 403/04; C07D 403/06; C07D 403/14; C07D 413/04; C07D 413/06; C07D 413/14; C07D 417/04; C07D 417/06; C07D 417/14

[52] U.S. Cl. .................................... 514/213; 549/523

[58] Field of Search ..................... 340/523; 514/213

[56] References Cited

U.S. PATENT DOCUMENTS

| | | | |
|---|---|---|---|
| 3,312,691 | 4/1967 | Wertner et al. | 540/523 |
| 3,330,823 | 7/1967 | Bernstein et al. | 540/461 |
| 3,562,257 | 2/1971 | Kugita et al. | 540/491 |
| 3,748,321 | 7/1973 | Krapcho | 540/455 |

OTHER PUBLICATIONS

Chemical Abstracts, vol. 106 (1987) Abstracting European Patent Application EP 205,334, published Dec. 17, 1985.
Reaction of 3-Phenylglycidic Esters IV[1]. Reaction of Methyl 3-(4-Methoxyphenyl)glycidate with 2-Nitrophenol and Synthesis of 1,5-Benzoxazepine Derivatives, Hashiyama et al. (Chem. Pharm. Bull.)

Primary Examiner—Robert T. Bond
Attorney, Agent, or Firm—Lawrence S. Levinson; Theodore R. Furman, Jr.

[57] ABSTRACT

Benzazepine derivatives useful, for example, as cardiovascular agents, are disclosed. These compounds have the general formula

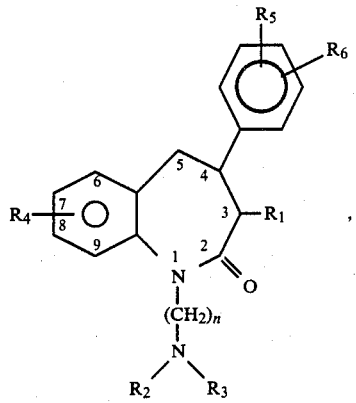

and pharmaceutically acceptable salts thereof.

20 Claims, No Drawings

3-SUBSTITUTED BENZAZEPINES

FIELD OF THE INVENTION

The present invention relates to benzazepine derivatives and more particularly concerns such compounds useful as cardiovascular agents.

SUMMARY OF THE INVENTION

In accordance with the present invention a novel class of benzazepine derivatives useful, for example, as cardiovascular agents, are disclosed. These compounds have the general formula

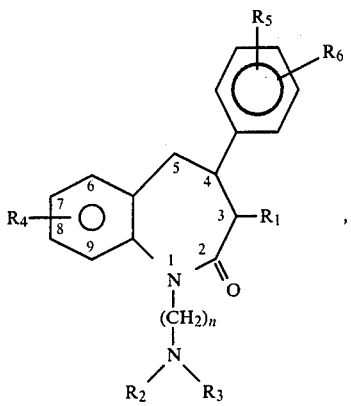

including pharmaceutically acceptable salts thereof, wherein

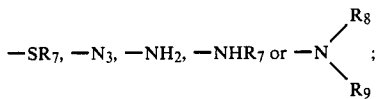

$R_2$ and $R_3$ are each independently hydrogen, alkyl, cycloalkyl or arylalkyl, or $R_2$ and $R_3$ together with the nitrogen atom to which they are attached are pyrrolidinyl, piperidinyl, or morpholinyl;

$R_4$, $R_5$ and $R_6$ are each independently hydrogen, halogen, alkyl, alkoxy, aryloxy, arylalkoxy, diarylalkoxy, arylalkyl, cyano, hydroxy, alkanoyloxy,

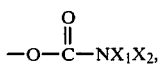

fluoro substituted alkoxy, fluoro substituted alkyl, (cycloalkyl)alkoxy, $-NO_2$, $-NX_3X_4$, $-S(O)_m$alkyl, $-S(O)_m$aryl,

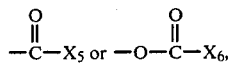

and $R_5$ and $R_6$ can be present in the ortho, meta or para positions;

$R_7$ is acyl, alkyl, aryl, or arylalkyl;

$R_8$ and $R_9$ are each independently hydrogen, alkyl, aryl, cycloalkyl or arylalkyl;

n is 2 or 3;

m is 0, 1 or 2;

$X_1$ and $X_2$ are each independently hydrogen, alkyl, aryl or heteroaryl, or $X_1$ and $X_2$ together with the nitrogen atom to which they are attached are pyrrolidinyl, piperidinyl or morpholinyl;

$X_3$ and $X_4$ are each independently hydrogen, alkyl, alkanoyl, arylcarbonyl, heteroarylcarbonyl, or

$X_5$ is hydroxy, alkoxy, aryloxy, amino, alkylamino or dialkylamino; and $X_6$ is alkyl, alkoxy or aryloxy;

with the proviso that if $R_4$ is a 7-alkyl group, it must have a tertiary carbon atom bonded to the ring.

DETAILED DESCRIPTION OF THE INVENTION

Listed below are definitions of various terms used to describe the benzazepines of this invention. These definitions apply to the terms as they are used throughout the specification (unless they are otherwise limited in specific instances) either individually or as part of a larger group.

The terms "alkyl" and "alkoxy" refer to both straight and branched chain groups. Those groups having 1 to 10 carbon atoms are preferred.

The term "alkenyl" refers to both straight and branched chain groups. Those groups having 2 to 10 carbon atoms are preferred.

The term "aryl" refers to phenyl and substituted phenyl. Exemplary substituted phenyl groups are phenyl groups substituted with 1, 2 or 3 amino ($-NH_2$), alkylamino, dialkylamino, nitro, halogen, hydroxyl, trifluoromethyl, alkyl (of 1 to 4 carbon atoms), alkoxy (of 1 to 4 carbon atoms), alkanoyloxy, carbamoyl, or carboxyl groups.

The term "alkanoyl" refers to groups having the formula alkyl

Those alkanoyl groups having 2 to 11 carbon atoms are preferred.

The term "heteroaryl" refers to an aromatic heterocyclic group having at least one heteroatom in the ring. Preferred groups are pyridinyl, pyrrolyl, imidazolyl, furyl, thienyl, or thiazolyl.

The term "cycloalkyl" refers to groups having 3, 4, 5, 6 or 7 carbon atoms.

The term "halogen" refers to fluorine, chlorine, bromine and iodine.

The terms "fluoro substituted alkyl" and "fluoro substituted alkoxy" refer to alkyl and alkoxy groups (as described above) in which one or more hydrogens have been replaced by fluorine atoms. Exemplary groups are trifluoromethyl, 2,2,2-trifluoroethyl, pentafluoroethyl, fluoromethoxy, difluoromethoxy, etc.

The compounds of formula I form acid-addition salts with inorganic and organic acids. These acid-addition salts frequently provide useful means for isolating the products from reaction mixtures by forming the salt in a medium in which it is insoluble. The free base may then be obtained by neutralization, e.g., with a base such as sodium hydroxide. Any other salt may then be formed from the free base and the appropriate inorganic or organic acid. Illustrative are the hydrohalides, especially the hydrochloride and hydrobromide, sulfate, nitrate, phosphate, borate, acetate, tartrate, maleate, fumarate, citrate, succinate, benzoate, ascorbate, salicylate, methanesulfonate, benzenesulfonate, toluenesulfonate and the like.

The carbon atoms in the 3 and 4-positions of the benzazepine nucleus of the compound of formula I are asymmetric carbons. The compounds of formula I, therefore, exist in enantiomeric and diastereomeric forms and as racemic mixtures thereof. All are within the scope of this invention. It is believed that those compounds of formula I which have the 3R, 4R configuration are the most potent and are therefore preferred.

The compounds of formula I can be prepared by first reacting a 2-nitrotoluene having the formula

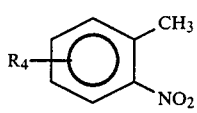

II with a benzylidine malonate having the formula

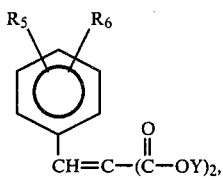

III wherein Y is alkyl. The reaction can be run in a polar nonprotic solvent (e.g., dimethylformamide), in the presence of a strong base such as sodium hydride, and yields a product having the formula

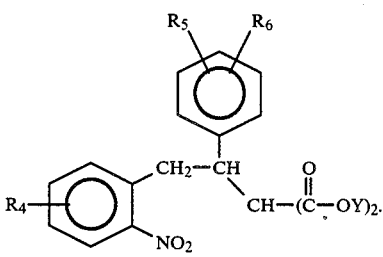

IV

Reduction of a compound of formula IV yields the corresponding compound having the formula

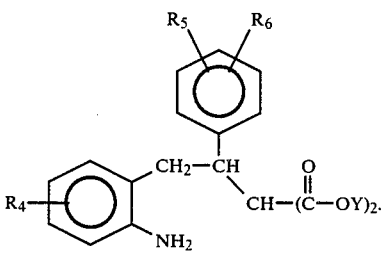

V

The reduction can be accomplished by catalytic hydrogenation (using, for example, palladium on charcoal as a catalyst) or using a chemical reducing agent (e.g., ferrous sulfate or stannous chloride).

Treatment of an amine of formula V with an alkali metal alkoxide (e.g., sodium methoxide) and an alcohol (e.g., methanol) yields the corresponding benzazepine having the formula

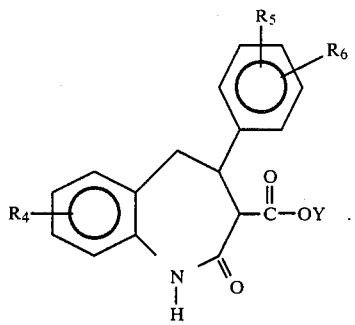

VI

Reaction of a compound of formula VI with a strong base (e.g., lithium diisopropylamide, potassium hexamethyldisilazide, or potassium t-amylate) in an etheral solvent, such as tetrahydrofuran, or a polar nonprotic solvent, e.g., dimethylformamide, at a low temperature in the presence of anhydrous oxygen gas and a reducing agent, e.g. triethyl phosphite, yields the corresponding compound having the formula

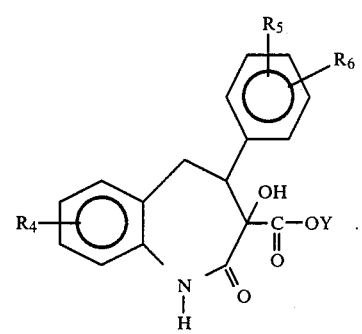

VII

Alternatively, a compound of formula VII can be prepared by first cooling a compound of formula VI to a greatly reduced temperature (e.g., about −78° C.) in a solvent such as tetrahydrofuran and treating it with a strong base (e.g., lithium diisopropylamide or potassium hexamethyldisilazide). Treatment of the compound with anhydrous oxygen gas in the presence of a reducing agent, such as triethyl phosphite, yields the desired compound of formula VII.

Decarboxylation of a compound of formula VII can be accomplished by treating the compound with excess lithium iodide in hot pyridine which contains 1–2% water to obtain a mixture of isomers having the formulas

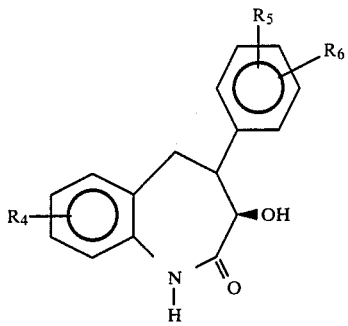

cis isomer and

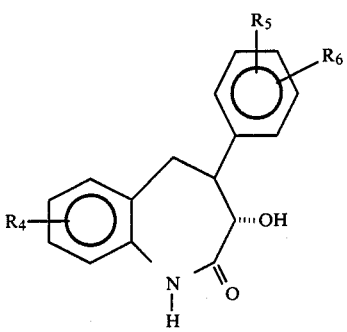

trans isomer

The preferred cis isomer is generally the predominant isomer formed during the above reaction. The isomers can be separated using art recognized techniques such as crystallization or chromatography. Alternatively, the reactions described hereinafter can be run using the diastereomeric mixture (mixture of compounds of formulas VIIIa and VIIIb). The isomeric mixture can be separated into its component isomers at any point during the reaction sequence.

Treatment of a mixture of compounds VIIIa and VIIIb with p-toluenesulfonylchloride in the presence of a solvent such as pyridine provides a mixture of compounds having the formula

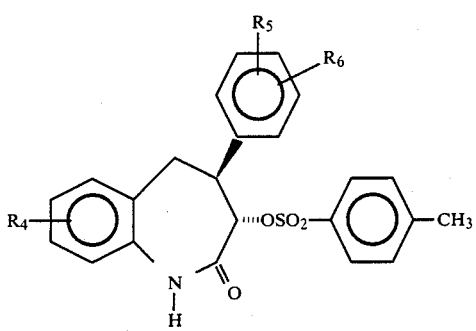

and the corresponding cis isomer

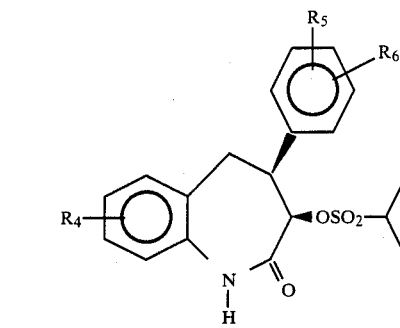

Thereafter, a mixture of compounds IXa and IXb in the presence of a solvent, e.g. dimethylsulfoxide, can be reacted with a compound of the formula $$MSR_7, \qquad X$$

(wherein M is a metal, such as Li, Na or K) such as sodium thiomethoxide where $R_7$ is methyl or potassium thioacetate thioacetate where $R_7$ is acetyl, to yield a mixture of compounds having the formula

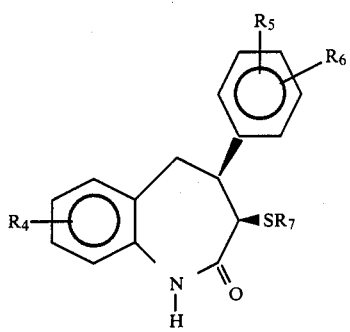

and

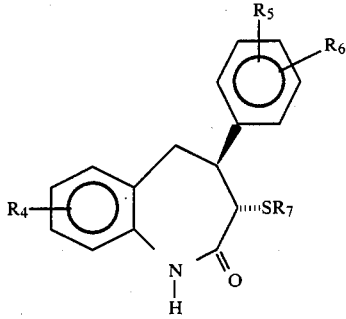

which can be separated using art recognized techniques such as crystallization and/or chromatography.

Treatment of the compound of formula XIa with solvents, such as methylethylketone or dimethylformamide, and a base, such as potassium hydrogen carbonate or sodium hydride, followed by reaction with a compound having the formula $$halogen-(CH_2)_n-NR_2R_3 \qquad XII$$

provides a compound of the formula

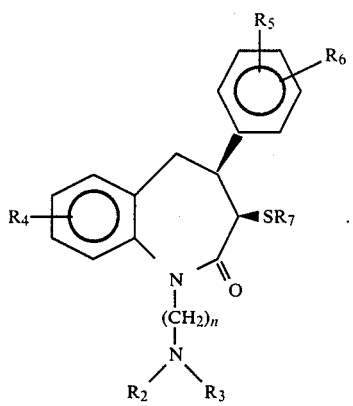

Similar treatment of the compound of formula XIb with a compound of formula XII under similar conditions provides the compound of the formula

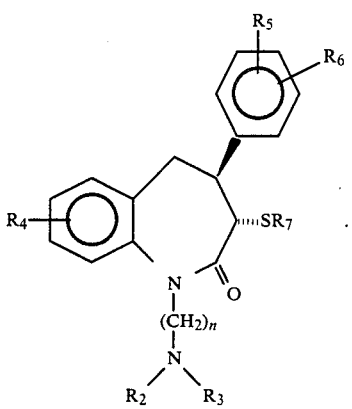

To prepare the compounds of formula I wherein $R_1$ is $N_3$, the trans isomer IXa in a solvent, e.g. dimethylformamide, can be reacted with sodium azide in the presence of an ammonium salt, such as tetra-n-butylammoniumhydrogen sulfate, to provide a diastereomeric mixture of the compounds having the formula

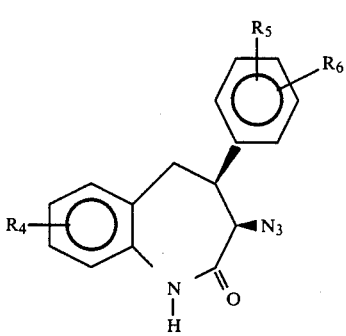

and

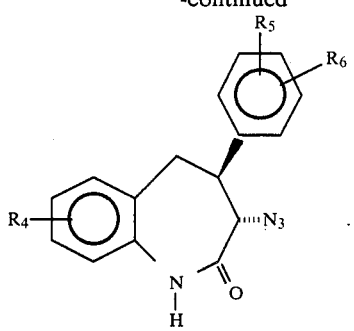

Treatment of compounds XIVa and XIVb with a base, such as potassium hydrogen carbonate, in a solvent, such as methylethylketone, followed by reaction with potassium iodide and a compound of formula XII, such as N,N-dimethyl-2-chloroethylamine, provides the compounds of formula I wherein $R_1$ is $N_3$ after separation of the isomers using art recognized techniques such as crystallization or chromatography.

To prepare the compounds of formula I wherein $R_1$ is $-NH_2$, a diastereomeric mixture of compounds VIIIa and VIIIb can be used as the starting material to ultimately provide the diastereomeric azide of the formula

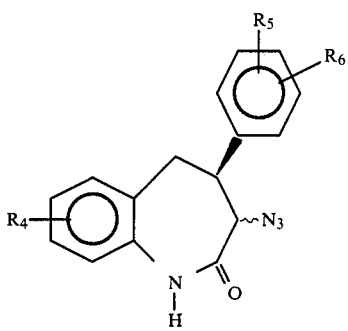

(i.e., the diastereomeric form of XIV) using the methodology outlined above.

Reduction of the azide XV, for example, by treatment with palladium-on-carbon in trifluoroacetic acid, provides

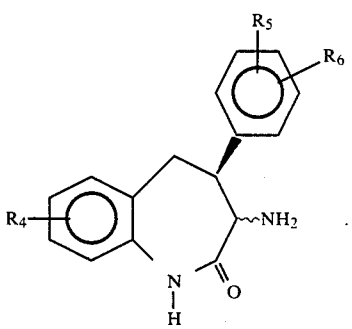

Compound XVI can be treated with di-t-butyl dicarbonate in presence of organic solvents, such as methylene chloride, acetonitrile and tetrahydrofuran and an organic base, such as pyridine to provide a diastereomeric mixture of compounds having the formula

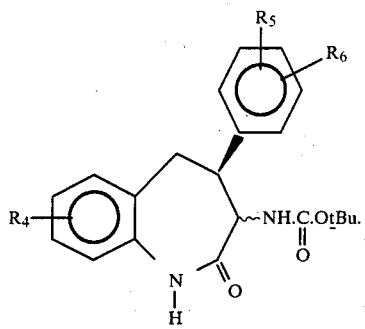

XVII

Compound XVII can be treated as Compounds XIVa and XIVb above to provide the compounds of formula I wherein $R_1$ is

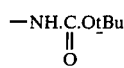

after separation of the diastereomers using art recognized techniques such as crystallization or chromatography. Compounds of formula I wherein $R_1$ is

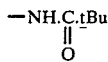

can be treated with trifluoroacetic acid in presence of anisole or thiophenol to provide the compounds of formula I wherein $R_1$ is $-NH_2$.

To prepare the compounds of the present invention wherein $R_1$ is $-NHR_7$ the amine of formula XVI can be subjected to an acid anhydride (such as acetic anhydride in the case where $R_7$ is acetyl) in the presence of organic solvents, such as methylene chloride and pyridine, to provide a diastereomeric mixture of compounds having the formula

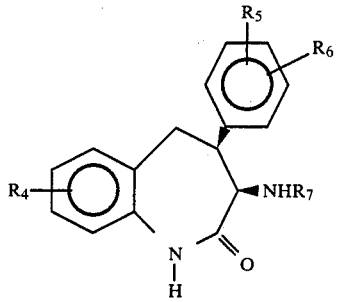

XVIIIa and

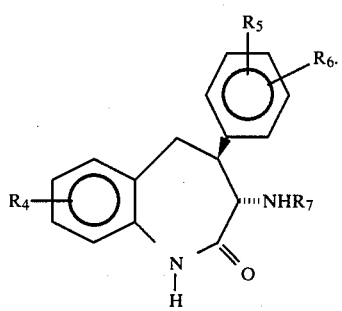

XVIIIb

Pure compound XVIIIa can be obtained from the mixture using art recognized separation techniques such as crystallization or chromatography.

Compound XVIIIa can be treated as compounds XIVa and XIVb above to provide the compounds of formula I wherein $R_1$ is $-NHR_7$.

To prepare compounds of formula I wherein $R_1$ is

a compound of formula IXa or IXb is heated in a sealed tube at a temperature ranging from 100°–150° C. with an amine of the formula

to provide compounds of formula

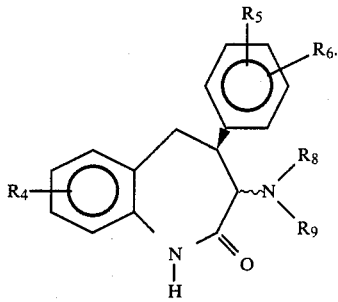

XIX

The isomers can be separated using art recognized techniques such as crystallization or chromatography. The pure cis-isomer of Compound XIX can be treated as compounds XIVa and XIVb above to provide the compounds of formula I wherein $R_1$ is

The resolved enantiomers of the compounds of this invention can be prepared by first hydrolyzing a compound of formula VI to obtain the corresponding carboxylic acid having the formula

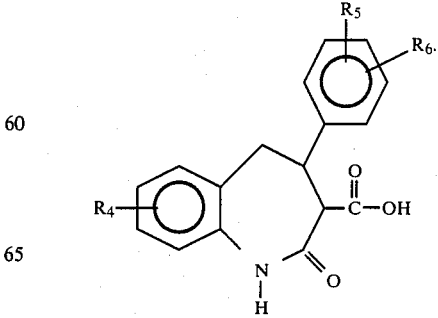

XX

The hydrolysis can be accomplished, for example, by treating a compound of formula VI with an alkali metal hydroxide in an alcohol (e.g., potassium hydroxide in methanol).

A carboxylic acid of formula XX can be resolved using a chiral amine. Reaction of the acid and amine in an appropriate solvent yields the diastereomeric salts which can be separated using conventional techniques such as crystallization. Regeneration of the carboxylic acid from the pure diastereomeric salt followed by esterification yields the desired nonracemic form of a compound of formula VI. Alternatively, compounds of formula VI can be generated directly from the diastereomeric salts by treatment with an alkyl halide in dimethylformamide in the presence of an inorganic base (e.g., potassium bicarbonate). This nonracemic compound can be converted to the corresponding nonracemic product of formula I via the nonracemic form of intermediates of formulas VII and VIII using the procedures described above.

Alternatively, the resolved enantiomers of the compounds of this invention can be prepared by the reaction of the various forms of formula I, prepared above, with a chiral carboxylic acid in an appropriate solvent. The resulting diastereomeric salts can be separated by recrystallization.

Preferred are those compounds of formula I wherein $R_1$ is —$SCH_3$, —S—acetyl and —$N_3$;

$R_2$ and $R_3$ are each methyl or $R_2$ is hydrogen and $R_3$ is methyl $R_4$ is trifluoromethyl (especially 7-trifluoromethyl and 6-trifluoromethyl);

$R_5$ is 4-methoxy; and, $R_6$ is hydrogen.

The compounds of formula I and the pharmaceutically acceptable salts thereof are useful as cardiovascular agents. These compounds act as vasodilators and are especially useful as anti-hypertensive agents. By the administration of a composition containing one (or a combination) of the compounds of this invention the blood pressure of a hypertensive mammalian (e.g, human) host is reduced. Daily doses of about 0.1 to 100 mg per kilogram of body weight per day, preferably about 1 to about 50 mg per kilogram per day, are appropriate to reduce blood pressure, and can be administered in single or divided doses. The substance is preferably administered orally, but parenteral routes such as the subcutaneous, intramuscular, or intravenous routes can also be employed.

As a result of the vasodilating activity of the compounds of formula I, it is believed that such compounds in addition to being anti-hypertensives may also be useful as anti-arrhythmic agents, as anti-anginal agents, as anti-fibrillatory agents, as anti-asthmatic agents, and in limiting myocardial infarction.

The compounds of this invention can also be formulated in combination with a diuretic or an angiotensin converting enzyme inhibitor. Suitable diuretics include the thiazide diuretics such as hydrochlorothiazide and bendroflumethiazide and suitable angiotensin converting enzyme inhibitors include captopril.

The present invention will be further described by reference to the following examples, however, it is not meant to be limited by the details described therein.

EXAMPLE 1

(trans)-1-[2-(Dimethylamino)ethyl]-1,3,4,5-tetrahydro-4-(4-methoxyphenyl)-3-(methylthio)-7-(trifluoromethyl)-2H-1-benzazeoin-2-one, monohydrochloride

A.

[2-(5-Trifluoromethyl-2-nitrophenyl)-1-(4-methoxyphenyl)ethyl]propanedioic acid, dimethylester To a 2 liter three-neck flask (under nitrogen) was added 67 g (0.293 mol) of dimethyl-p-methoxybenzylidene malonate and 450 ml of dimethylformamide. The stirred solution was treated with a 50% sodium hydride dispersion (18.7 g, 0.39 mol). This mixture was treated dropwise with a solution of 3-methyl-4-nitrobenzoic acid (60.5 g, 0.293 mol) in 50 ml of dimethylformamide over a period of 1 hour while maintaining a temperature at about 28°–32° C. This mixture was stirred for 4 hours at room temperature, cooled, treated portionwise with 25 ml of acetic acid and poured onto a 2.5 l of ice water. The mixture was extracted 3 times with 250 ml of methylene chloride. The organic phases were combined, washed 3 times with 500 ml of water, dried over anhydrous magnesium sulfate, filtered and the solvent evaporated to give 126 g of a pale brown semi-solid. The latter was dissolved in 270 ml of methanol, cooled and filtered to give 72.8 g of a pale yellow product, m.p. 110°–112° C. A sample recrystallized from methanol, melted at 111°–113° C.

Analysis calc'd for $C_{21}H_{20}NF_3O_7$:

C, 55.39; H, 4.43; N, 3.08; F, 12.52;

Found: C, 56.08; H, 4.70; N, 2.96; F, 12.09.

B.

[2-(5-Trifluoromethyl-2-aminophenyl)-1-(4-methoxyphenyl)ethyl]propanedioic acid, dimethylester A suspension of the title A compound (25 g, 0.055 mol) in 200 ml of methanol was treated with a cold suspension of 2.5 g of 5% palladium-on-carbon in 50 ml of methanol (under nitrogen) and placed on the Parr apparatus at 58 psi of hydrogen. After 30 minutes, the mixture was heated at 50°–55° for 1 hour, cooled to room temperature, removed from the Parr apparatus and allowed to stand at room temperature overnight. The flask was heated to dissolve the crystallized product and the hot solution was filtered through Celite (under nitrogen) and washed with hot methanol. The colorless filtrate was concentrated on a rotary evaporator to give 22.2 g of a nearly colorless solid. The latter was triturated with 100 ml of hexane and then with 50 ml of hexane. The solvent was decanted and the entrained solvent removed on a rotary evaporator to give 21.3 g of product, m.p. 124°–127° C. A sample of this material, after crystallization from methanol, melted at 125°–127° C.

Analysis calc'd for $C_{21}H_{22}NF_3O_5$:

C, 59.2; H, 5.2; N, 3.2; F, 13.40;

Found: C, 59.48; H, 5.26; N, 3.16; F, 13.43.

7-(Trifluoromethyl)-1,3,4,5-tetrahydro-3-(methoxycarbonyl)-4-(4-methoxyphenyl)-2H-1-benzazepin-2-one A stirred solution of the title B compound (20 g, 0.047 mol) in 200 ml of methanol was treated with 13.3 ml of 25% sodium methoxide in methanol and heated to reflux (color lightened progressively from reddish to light yellow; also some solid separated during the heating). TLC (1:1 ethyl acetate/hexane) after 2.5 hours showed the reaction to be essentially complete. After a total of 2.75 hours of heating, the mixture was cooled in ice water and 70 ml of 1N hydrochloric acid was added to precipitate the partly gummy product. The latter became granular on rubbing and stirring in an ice water bath for 0.5 hours. The tan solid was filtered, washed with water and air dried to give 10.0 g of a pale yellow foam-like material. The latter was suspended in 30 ml of isopropyl alcohol, allowed to stand for 1 hour, filtered and washed with isopropyl alcohol and hexane to provide 13.64 g of the title C compound, m.p. 161°–163° C.

Analysis calc'd for $C_{20}H_{18}NF_3O_4$:
C, 61.07; H, 4.61; N, 3.56; F, 14.49;
Found: C, 61.26; H, 4.62; N, 3.41; F, 14.21.

D.
7-(Trifluoromethyl)-1,3,4,5-tetrahydro-3-hydroxy-3-(methoxycarbonyl)-4-(4-methoxyphenyl)-2H-1-benzazepin-2-one A solution of the title C compound (7 g, 0.0178 mol) in 330 ml of dry tetrahydrofuran was cooled to −78° C. and a 1.125M solution of potassium hexamethyldisilazide (64 ml, 0.072 mol) in tetrahydrofuran was added dropwise over 15 minutes. After stirring for 1 hour, 12.4 ml of triethylphosphite (0.0723 mol) was added and oxygen was bubbled rapidly through the resulting solution. The reaction temperature was then raised to 0° C. and allowed to stir for 2 hours. Oxygenation was then discontinued and the reaction was quenched by addition of acetic acid. The reaction mixture was then concentrated and the residue was dissolved in ethyl acetate. The organic solution was washed successively with 1N hydrochloric acid, saturated sodium bicarbonate and brine and then dried over anhydrous sodium sulfate. Concentration of the organic extract, followed by trituration with 200 ml of hexane afforded 7 g of pale cream-colored solid; m.p. 196°–198° C.

Analysis calc'd for $C_{20}H_{18}F_3NO_5 \cdot H_2O$:
C, 56.20; H, 4.72; N, 3.28;
Found: C, 56.39; H, 4.37; N, 3.13.

E.
7-(Trifluoromethyl)-1,3,4,5-tetrahydro-3-hydroxy-4-(4-methoxyphenyl)-2H-1-benzazepin-2-one A solution of the title D compound (6.8 g, 0.0166 mol) and lithium iodide (5.8 g, 0.0433 mol) in 250 ml of pyridine was refluxed under argon for 2 hours. The reaction was cooled to room temperature and concentrated in vacuo. The residue was dissolved in ethyl acetate and extracted with 1N hydrochloric acid, saturated sodium bicarbonate and sodium chloride. The solution was dried over anhydrous magnesium sulfate, filtered and concentrated to obtain 5.3 g of crude solid which was triturated with 120 ml of ether at 0° C. to obtain 4.45 g of colorless material, m.p. 204°–206° C. TLC (1:1 ethyl acetate-hexane) showed an approximate 60:40 ratio of cis and trans-products.

Analysis calc'd for $C_{18}H_{16}F_3NO_3$:
C, 61.53; H, 4.59; N, 3.99;
Found: C, 61.37; H, 4.57; N, 3.93.

F.
7-(Trifluoromethyl)-1,3,4,5-tetrahydro-3-(p-toluenesulfonyloxy)-4-(4-methoxyphenyl)-2H-1-benzazepin-2-one To a solution of the title E compound (12.53 g, 36 mmole) in pyridine (60 ml) was added 99% pure p-toluenesulfonylchloride (8.98 g, 47.1 mmole) with stirring. After standing at room temperature for 24 hours, the mixture was diluted with ethyl acetate and washed thoroughly with saturated copper sulfate solution, followed by water. The organic extract was dried over anhydrous magnesium sulfate and concentrated. The oily residue was triturated with ether to obtain a white precipitate that was collected by suction-filtration, and washed with ether:hexane 1:3. After drying in vacuo 16.87 g of a 1:1 -cis:trans mixture of the title F compound was obtained as a white solid.

G.
(trans)-3-Thiomethyl-7-(trifluoromethyl)-1,3,4,5-tetrahydro-4-(4-methoxyphenyl)-2H-1-benzazepin-2-one
and
(cis)-3-Thiomethyl-7-(trifluoromethyl)-1,3,4,5-tetrahydro-4-(4-methoxyphenyl)-2H-1-benzazepin-2-one To a solution of the title F compound in dimethylsulfoxide (50 ml) was added solid sodium thiomethoxide (3.15 g, 45 mmole) with stirring under an argon atmosphere. The mixture was heated (bath temperature 80°–90° C.) for 0.5 hour, cooled, diluted with ethyl acetate and washed thoroughly with 1N aqueous hydrochloric acid solution, followed by water. The ethyl acetate extract was dried over anhydrous magnesium sulfate and concentrated leaving a dark, oily residue. Ether trituration afforded a white crystalline material, which was collected by suction-filtration and washed with ether:hexane 1:3 to give 6.89 g of 1:1 -cis:trans mixture of product. Recrystallization gave 1.27 g of pure trans of the title G compound; m.p. 232°–233.5° C.

Analysis calc'd for $C_{19}H_{18}NF_hd 3O_2S$:
C, 59.83; H, 4.76; N, 3.67; F, 14.94;
S, 8.41;
Found: C, 60.17; H, 4.80; N, 3.66; F, 14.75;
S, 8.82.

Purification of the mother liquor by chromatography on a silica-gel column with 1:1 ethyl acetate:hexane as eluent afforded 620 mg cis-adduct.

H.
(trans)-1-[2-(Dimethylamino)ethyl]-1,3,4,5-tetrahydro-4-(4-methoxyphenyl)-3-(methylthio)-7-(trifluoromethyl)-2H-1-benzazepin-2-one, monohydrochloride To a homogeneous solution of the title G trans compound (1.29 g, 3.38 mmole) in hot methylethyl-ketone (16 ml) and dimethylformamide (3 ml) under argon was added potassium hydrogen carbonate (1.35 g; 13.5 mmole; 4 eq). After stirring for 15 minutes, a 2.15M toluene solution of N,N-dimethyl-2-chloroethylamine (3.1 ml, 6.8 mmole, 2 eq) was added, and heating was continued for 4 hours. The mixture was cooled, diluted with ethyl acetate, washed consecutively with water, 1N sodium hydrogen carbonate, and saturated sodium chloride, and dried over anhydrous magnesium sulfate. The ethyl acetate solution was then treated with saturated hydrochloric acid/ethyl ether and concentrated. The off-white solid was triturated and vacuum-dried leaving 1.34 g of the title compound as a white solid; m.p. 230°–231° C.

Analysis calc'd for $2_{23}H_{28}N_2ClF_3O_2S \cdot 0.07H_2O$:
C, 56.36; H, 5.78; N, 5.72; Cl, 7.23
F, 11.62; S, 6.54;
Found: C, 56.08; H, 5.78; N, 5.74; Cl, 7.20;
F, 11.92; S, 6.74.

EXAMPLE 2

(cis)-1-[2-(Dimethylamino)ethyl]-1,3,4,5-tetrahydro-4-(4-methoxyphenyl)-3-(methylthio)-7-trifluoromethyl)-2H-1-benzazepin-2-one, monohydrochloride To a homogeneous solution of Example 1, Part G cis-compound (0.62 g, 1.51 mmol) in methylethylketone (8 ml) and dry dimethylformamide (4 ml) was added potassium hydrogen carbonate (0.60 g, 6.0 mmol; 4 eq). After stirring for 15 minutes at 90°, a 2.15M toluene solution of N,N-dimethyl-2-chloroethylamine (1.4 ml, 3.0 mmol; 2 eq) was added and heating was continued for 5.75 hours. The solution was cooled, diluted with ethyl acetate and washed with water. The organic extract was dried over anhydrous magnesium sulfate, filtered and concentrated. The free amine was purified by preparative plate chromatography (silica gel, eluting solvent 5% methanol in methylene chloride), dissolved in warm ether and treated with etheral hydrochloric acid solution to obtain 350 mg of a white solid, m.p. 160°–164° C.

Analysis calc' for $C_{23}H_{28}N_2ClF_3O_2S \cdot 0.58H_2O$:
C, 55.31; H, 5.89; N, 5.61; Cl, 7.10;
F, 11.41; S, 6.42;
Found: C, 55.28; H, 5.74; N, 5.64; Cl, 7.01;
F, 11.56; S, 6.41.

EXAMPLE 3

(cis)-3-(Acetylthio)-1-[2-(dimethylamino)ethyl]-1,3,4,5-tetrahydro-4-(4-methoxyphenyl)-7-(trifluoromethyl)-2H-1-benzazepin-2-one, monohydrochloride

A.
(cis)-3-(Acetylthio)-7-(trifluoromethyl)-1,3,4,5-tetrahydro-4-(4-methoxyphenyl)-2H-benzazepin-2-one To a solution of the epimeric mixture of the tosylate of Part F of Example 1 (1.06 g, 2 mmole) in 10 ml dimethylsulfoxide was added with stirring potassium thioacetate (570 mg, 5 mmole) under an argon atmosphere. The reaction mixture was heated to 90° C. and left at that temperature for 1 hour. The reaction was cooled, diluted with ethyl acetate and washed thoroughly with water. The ethyl acetate, extract was dried over anhydrous magnesium sulfate and concentrated under reduced pressure to obtain a yellow residue. Trituration with ether gave almost pure cis-thioacetate (215 mg) as a white crystalline solid. A combination of flash chromatography and recrystallization gave analytically pure product; m.p. 215°–215.5° C.

Analysis calc'd for $C_{20}H_{18}NF_3O_3S \cdot 0.25H_2O$: C, 58.03; H, 4.51; N, 3.38; S, 7.75; F, 13.76; Found: C, 58.06; H, 4.30; N, 3.35; S, 8.09; F, 13.94.

B.
cis-3-(Acetylthio)-1-[2-(dimethylamino)ethyl]-1,3,4,5-tetrahydro-4-(4-methoxyphenyl)-7-(trifluoromethyl)-2H-1-benzazepin-2-one, monohydrochloride The reaction was run as described in Example 1, Part H except that the compound from Part B of Example 3 (740 mg, 1.81 mmole) was substituted for the compound of part G of Example 1. The crude free amine was purified by preparative plate chromatography (silica gel, eluting solvent 10% methanol in methylene chloride) and then treated with etheral hydrochloric acid solution to obtain 500 mg of a white solid; m.p. 147.5°–150.5° C.

Analysis calc'd for $C_{24}H_{27}N_2F_3O_3S \cdot HCl \cdot 0.69H_2O$: C, 54.45; H, 5.59; N, 5.29; Cl, 6.70; S, 6.06; Found: C, 54.45; H, 5.46; N, 5.42; Cl, 6.94; S, 6.28.

EXAMPLE 4

(cis)-3-Azido-7-chloro-1-[2-(dimethylamino)ethyl]-1,3,4,5-tetrahydro-4-(4-methoxyphenyl)-2H-1-benzazepin-2-one, monohydrochloride

A.
[2-(5-Chloro-2-nitrophenyl)-1-(4-methoxyphenyl)ethyl]propanedioic acid, dimethylester To a stirred mixture of dimethyl p-methoxybenzylidene malonate (40 g, 0.16 mole) and 60% dispersion of sodium hydride (9.6 g, 0.24 mole) in 350 ml of dry dimethylformamide, was added dropwise over 2 hours a solution of 5-chloro-2-nitrotoluene (30 g, 0.176 mole) in 30 ml of dimethylformamide. The reaction was stirred at room temperature for 6 hours, then quenched with glacial acetic acid (15.4 ml, 0.26 mole). The solvent was removed in vacuo and the residue was triturated with water. The yellow solids were filtered and triturated with methanol to yield 50.3 g of a white solid, melting point 128.5°–130.5° C.

B.
[2-(2-Amino-5-chlorophenyl)-1-(4-methoxyphenyl)ethyl]propanedioic acid, dimethylester To a refluxing mixture of [2-(5-chloro-2-nitrophenyl)-1-(4-methoxyphenyl)ethyl]propanedioic acid, dimethyl ester (40 g, 95 mmole) and hydrated ferrous sulfate (184.5 g, 0.663 mole) in a 1:10 solution of methanol:water (1.2 L) was added concentrated ammonium hydroxide (142.5 ml) over a 30 minute period. The reaction was stirred at reflux for 20 minutes then cooled to room temperature. Ethyl acetate and Celite were added and the mixture was filtered through Celite. The filtrate was partitioned between ethyl acetate and water. The organic phase was dried over magnesium sulfate and concentrated in vacuo. The product was recrystallized from isopropyl alcohol to yield 28.22 g of the title compound, melting point 114°–116° C.

C.
7-Chloro-1,3,4,5-tetrahydro-3-(methoxycarbonyl)-4-(4-methoxyphenyl)-2H-1-benzazepin-2-one To a solution of [2-(2-amino-5-chlorophenyl)-1-(4-methoxyphenyl)ethyl]propanedioic acid, dimethyl ester (23.2 g, 59.2 mmole) in methanol (200 ml) was added a 25% solution of sodium methoxide in methanol (16 ml, 69.97 mmole). The solution was refluxed for 3 hours under argon. The reaction was cooled to room temperature and treated with 200 ml of 1N hydrochloric acid. The white precipitate was filtered and washed with water, methanol, and dried in vacuo to yield 19.5 g of the title compound, melting point 189°–190.5° C.

D.
7-Chloro-1,3,4,5-tetrahydro-3-hydroxy-3-(methoxycarbonyl)-4-(4-methoxyphenyl)-2H-1-benzazepin-2-one A solution of 7-chloro-1,3,4,5-tetrahydro-3-(methoxycarbonyl)-4-(4-methoxyphenyl)-2H-1-benzazepin-2-one (15 g, 41.7 mmole) in 780 ml of tetrahydrofuran was cooled to −78° C. and 147 ml (167 mmole in tetrahydrofuran) of potassium hexamethyldisilazide solution was added. After stirring for 1 hour, 28.7 ml of triethyl phosphite (166.7 mmole) was added and anhydrous oxygen gas was rapidly bubbled through the resulting solution. The reaction temperature was then raised to 0° C. and allowed to stir for an additional hour. Oxygenation was then discontinued and the reaction was quenched by the addition of 50 ml of acetic acid. The reaction mixture was then concentrated and the residue dissolved in ethyl acetate. The organic solution was washed successively with 1N hydrochloric acid, saturated sodium bicarbonate, and brine and then dried over anhydrous sodium sulfate. Concentration of the dried organic solution afforded a solid which, upon trituration in hexane, gave 14.8 g of the title compound.

E.
(trans)-7-Chloro-1,3,4,5,-tetrahydro-3-hydroxy-4-(4-methoxyphenyl)-2H-1-benzazepin-2-one A solution of lithium iodide (1.42 g, 10.6 mmole; 4 eq) in pyridine (27 ml) and benzene (27 ml) were distilled under argon until pyridine started to distill over. Title D compound (1 g, 2.66 mmole) was added and the reaction mixture was refluxed for 8 hours to maximize the yield of the trans product. The reaction mixture was cooled to room temperature, diluted with ethyl acetate and washed with 1N hydrochloric acid solution. The aqueous layer was extracted twice with ethyl acetate. Combined organic extract was washed with saturated sodium bicarbonate solution, dried over anhydrous sodium sulfate, filtered and concentrated to obtain 890 mg of a tan solid. TLC indicated a trans/cis ratio of 75:25. Purification by chromatography on a silica-gel column and elution with 25-75% ethyl acetate in hexane furnished 420 mg of a sticky yellow solid which on trituration with ether and etyl acetate gave 180 mg of a white solid, m.p. 161.5°-162.5° C.

Analysis calc'd for $C_{17}H_{16}ClNO_3 \cdot 0.14H_2O$: C, 63.74; H, 5.12; N, 4.37; Cl, 11.07; Found: C, 63.80; H, 5.12; N, 4.35; Cl, 11.12.

F.
(trans)-7-Chloro-1,3,4,5-tetrahydro-3-(p-toluenesulfonyloxy)-4-(4-methoxyphenyl)-2H-1-benzazepin-2-one Tosyl chloride (204 mg, 1.07 mmole; 2 eq) and pyridine (2 ml) were added to the title E compound (160 mg, 0.503 mmole) and stirred at room temperature for 3 hours. The mixture was diluted with ethyl acetate, washed with saturated copper sulfate followed by water and dried over anhydrous magnesium sulfate, filtered and concentrated. The concentrated crude product was purified by flash chromatography giving 250 mg of the title F compound as a white solid product.

G.
(cis)-3-Azido-7-chloro-1,3,4,5,-tetrahydro-4-(4-methoxyphenyl)-2H-1-benzazepin-2-one Sodium azide (120 mg, 1.54% mmole, 5 eq) and tetra-n-butyl ammonium hydrogen sulfate (54 mg) were added to a solution of the title F compound (150 mg, 0.31 mmole) in dimethylformamide (2 ml). The mixture was stirred at 80° C. for 8 hours. The cooled solution was diluted with ethyl acetate, washed with water, dried over anhydrous magnesium sulfate and concentrated. The crude residue was triturated with ethyl acetate giving 46 mg of clean title C compound. The material in the mother liquor was purified by flash chromatography yielding an additional 15 mg of the title G compound and 50 mg of recovered starting material.

H.
(cis)-3-Azido-7-chloro-1-[2-(dimethylamino)ethyl]-1,3,4,5-tetrahydro-4-(4-methoxyphenyl)-2H-1-benzazepin-2-one, monohydrochloride To the title G compound (0.85 g, 2.48 mmole), potassium hydrogen carbonate (0.50 g, 4.96 mmole) and potassium iodide (0.10 g, 0.62 mmole) suspended in methylethylketone (20 ml), was added 1.86 ml (3.16 mmole) of 1.7N solution of 2-dimethylaminoethylchloride in toluene with stirring. The mixture was refluxed (85° C.) for 12 hours. The cooled solution was evaporated almost to dryness, diluted with ethyl acetate and washed twice with water, saturated sodium chloride and dried over anhydrous magnesium sulfate. The concentrated residue was flash chromatographed giving an oily residue. This material was co-evaporated with ether which produced a fluffy white solid. The free amine product was dissolved into ether and treated with ethereal hydrogen chloride to give 0.64 g of the title compound as an hygroscopic white solid; m.p. 183°-193° C. (decomp).

Analysis calc'd for $C_{21}H_{24}N_5ClO_2 \cdot 0.8H_2O$: C, 54.30; H, 5.77; N, 14.84; Cl, 15.27; Found: C, 54.30; H, 5.47; N, 15.08; Cl, 15.23.

EXAMPLE 5

(cis)-3-Azido-1-[2-(dimethylamino)ethyl]-1,3,4,5-tetrahydro-4-(4-methoxyphenyl)-7-(trifluoromethyl)-2H-1-benzazepin-2-one, monohydrochloride

A.
(trans)-7-(Trifluoromethyl)-1,3,4,5-tetrahydro-3-hydroxy-4-(4-methoxyphenyl)-2H-1-benzazepin-2-one The Example 1, Part E alcohol (6.6 g, 60:40 cis:trans) was purified on a silica gel column with 1:9 ethyl acetate:hexane as eluent to obtain 1.77 g pure title A trans-alcohol.

B.
(trans)-7-(Trifluoromethyl)-1,3,4,5-tetrahydro-3-(p-toluenesulfonyloxy)-4-(4-methoxyphenyl)-2H-1-benzazepin-2-one To the Example 5, Part A alcohol (1.77 g, 5.04 mmole) in pyridine (15 ml) was added p-toluene- sulfonyl chloride (1.92 g, 10.08 mmole; 2 eq). The reaction mixture was stirred at room temperature overnight, diluted with ethyl acetate, and washed with saturated cooper sulfate solution (2X), water and saturated salt solution. The organic extract was dried over anhydrous magnesium sulfate, filtered and concentrated to obtain 2.88 g of a pink solid. Purification by chromatography on a silica gel column and elution with 25-50% ethyl acetate in hexane followed by ethyl acetate and 1% acetone in ethyl acetate afforded 2.22 g of a white solid.

C.
3-Azido-7-(trifluoromethyl)-1,3,4,5-tetrahydro-4-(4-methoxyphenyl)-2H-1-benzazepin-2-one Sodium azide (1.68 g, 25.86 mmole, 6 eq) was added to a solution of title A compound (2.22 g, 4.3 mmole) and tetra-n-butyl ammonium hydrogen-sulfate (0.73 g, 2.15 mmole, 0.5 eq). After heating at 80° C. overnight, the mixture was partitioned between ethyl acetate and water. The aqueous layer was extracted with ethyl acetate and combined extracts were dried over anhydrous magnesium sulfate, filtered and concentrated to obtain 3.83 g of a viscous yellow oil which was purified on a silica gel column to obtain 1.14 g of a solid. TLC indicated it to be a 1:1 mixture of cis and trans compound.

D.

cis-3-Azido-1-[2-(dimethylamino)ethyl]-1,3,4,5-tetrahydro-4-(4-methoxyphenyl)-7-(trifluoromethyl)-2H-1-benzazepin-2-one, monohydrochloride Title C compound (430 mg, 1.14 mmole) in methylene chloride (10 ml) and water (1.5 ml) was treated with pulverized barium hydroxide octahydrate (0.75 g, 2.39 mmole) and benzyltrimethylammonium chloride (catalytic). 2-dimethylamino ethyl bromide (0.60 g, 2.57 mmole) in water (2 ml) was added with vigorous stirring. After stirring at room temperature overnight, the reaction mixture was partitioned between methylene chloride and water. The organic layer was washed successively with water, 1N hydrochloric acid, saturated sodium hydroxide and saturated salt solution. The organic layer was dried over anhydrous magnesium sulfate, filtered and concentrated. The free amine was purified on a silica gel column. The pure cis-amine was dissolved in ether and treated with etheral hydrogen chloride to obtain 540 mg of a white solid; m.p. 195°–197° C.

Analysis calc'd for $C_{22}H_{25}F_3N_5O_2Cl \cdot 0.62H_2O$: C, 53.36; H, 5.34; N, 14.14; Cl, 7.16; F, 11.51; Found: C, 53.36; H, 5.26; N, 13.72; Cl, 7.10; F, 11.29.

EXAMPLE 6

(cis)-3-(Acetylamino)-1-[2-(dimethylamino)ethyl]-1,3,4,5-tetrahydro-4-(4-methoxyphenyl)-7-(trifluoromethyl)-2H-1-benzazepin-2-one, monohydrochloride

A.

7-(Trifluoromethyl)-1,3,4,5-tetrahydro-3-amino-4-(4-methoxyphenyl)-2H-1-benzazepin-2-one The azide of part B of Example 5 (870 mg, 2.31 mmole) was catalytically reduced with 10% palladium-on-carbon (163 mg) in trifluoroacetic acid (40 ml). After 2 hours, the mixture was filtered through a pad of celite. The solid residue was rinsed with ethyl acetate and the combined filtrate was concentrated. The residue was dissolved in ethyl acetate and washed twice with 1N sodium hydrogen carbonate, followed by saturated sodium chloride, dried over anhydrous magnesium sulfate, and concentrated to give 800 mg of an off-white solid which was triturated with ether and vacuum-dried to obtain 660 mg of the title A compound.

B.

(cis)-(3-Acetylamino)-7-(trifluoromethyl)-1,3,4,5-tetrahydro-4-(4-methoxyphenyl)-2H-1-benzazepin-2-one Acetic anhydride (2 ml) was added to the amine of the title A compound (100 mg, 0.285 mmole) in methylene chloride (3 ml) and pyridine (3 ml). Stirring was continued for about 5 hours. The mixture was diluted with methylene chloride and washed three times with 1N hydrochloric acid, dried over anhydrous magnesium sulfate, and concentrated. The oily residue was placed under high vacuum overnight to obtain 100 mg of a white solid which was flash chromatographed to give 50 mg of the title B pure cis-compound as a white solid.

C.

(cis)-3-(Acetylamino)-1-[2-(dimethylamino)ethyl]-1,3,4,5-tetrahydro-4-(4-methoxyphenyl)-7-(trifluoromethyl)-2H-1-benzazepin-2-one, monohydrochloride Potassium hydrogen carbonate (300 mg, 2.96 mmole), the title B compound (580 mg, 1.48 mmole), and potassium iodide were suspended in methylethylketone (25 ml). A 2.15M toluene solution of N,N-dimethylaminoethyl chloride (1 ml, 2.22 mmole) was added with stirring, and the mixture was refluxed for 4 hours. Another 1 ml of N,N-dimethylaminoethyl chloride solution was added, and reflux was continued for an additional 3 hours. The solvent was evaporated and the residue was dissolved in ethyl acetate, washed with water, dried over anhydrous magnesium sulfate, and concentrated giving 0.56 g of a tan semisolid. This crude material was flash chromatographed to give 400 mg of free amine which was dissolved in ether, and treated with saturated ethereal hydrochloric acid. The off-white solid was collected by suction filtration and then triturated with ether (X2) to yield 340 mg of the title compound; m.p. 192°–196° C.

Analysis calc'd for $C_{24}H_{29}F_3N_3O_3Cl \cdot 1.25H_2O$: C, 55.17; H, 6.07; N, 8.04; Cl, 6.79; F, 10.9; Found: C, 55.17; H, 5.77; N, 7.84; Cl, 6.66; F, 10.5.

EXAMPLES 7 TO 30

Following the procedures described above and as outlined in Examples 1–6, the following additional compounds within the scope of the present invention can be made.

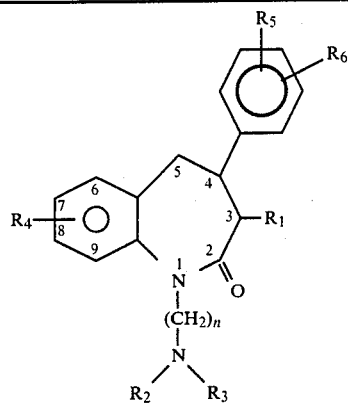

| Ex. No. | R₁ | R₂ | R₃ | R₄ | R₅ | R₆ | n |
|---|---|---|---|---|---|---|---|
| 7 | —SC$_2$H$_5$ | —CH$_3$ | —CH$_3$ | 7-CF$_3$ | 4-OCH$_3$ | —H | 2 |
| 8 | —S—C$_6$H$_5$ | —CH$_3$ | —CH$_3$ | 7-CF$_3$ | 4-OCH$_3$ | —H | 3 |
| 9 | —S—C(=O)CH$_3$ | —CH$_3$ | —CH$_3$ | 6-CF$_3$ | 4-OCH$_3$ | —H | 2 |
| 10 | —S—CH$_2$—C$_6$H$_5$ | —CH$_3$ | —CH$_3$ | 7-CF$_3$ | 4-OCH$_3$ | —H | 2 |
| 11 | —SC$_3$H$_7$ | —CH$_3$ | —CH$_3$ | 7-CF$_3$ | 4-OCH$_3$ | —H | 2 |
| 12 | —SCH$_3$ | \multicolumn{2}{c}{pyrrolidino} | 7-CF$_3$ | 4-OCH$_3$ | —H | 2 |
| 13 | —N=N≡N | \multicolumn{2}{c}{morpholino} | 7-CF$_3$ | 4-OCH$_3$ | —H | 3 |
| 14 | —NH—C(=O)CH$_3$ | \multicolumn{2}{c}{piperidino} | 7-CF$_3$ | 4-OCH$_3$ | —H | 2 |
| 15 | —NH$_2$ | —CH$_3$ | —CH$_3$ | 7-CF$_3$ | 4-OCH$_3$ | —H | 2 |
| 16 | —NH—C$_6$H$_5$ | —CH$_3$ | —CH$_3$ | 7-CF$_3$ | 4-OCH$_3$ | —H | 2 |
| 17 | —NH—CH$_2$—C$_6$H$_5$ | —CH$_3$ | —CH$_3$ | 7-CF$_3$ | 4-OCH$_3$ | —H | 2 |
| 18 | —NHCH$_3$ | —CH$_3$ | —CH$_3$ | 7-CF$_3$ | 4-OCH$_3$ | —H | 2 |

-continued

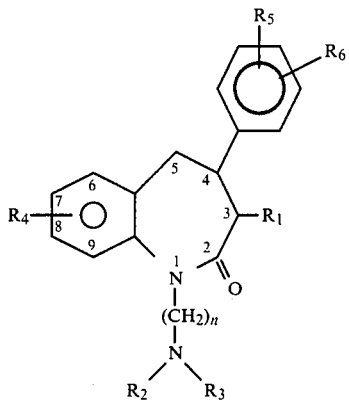

| Ex. No. | R₁ | R₂ | R₃ | R₄ | R₅ | R₆ | n |
|---|---|---|---|---|---|---|---|
| 19 | $-N(CH_3)_2$ | $-CH_3$ | $-CH_3$ | 7-Cl | 3-C≡N | 4-OCH₃ | 2 |
| 20 | $-N(CH_3)(CH_2C_6H_5)$ | $-CH_3$ | $-CH_3$ | 6-CF₃ | 4-Br | $-H$ | 3 |
| 21 | $-SCH_3$ | $-CH_3$ | $-CH_3$ | 6-NO₂ | 4-O-C(O)-NH₂ | 3-CH₃ | 2 |
| 22 | $-S-C(O)CH_3$ | $-CH_3$ | $-CH_3$ | 7-NO₂ | 4-SO₂CH₃ | $-H$ | 3 |
| 23 | $-S-C(O)CH_3$ | $-H$ | $-CH_3$ | 7-CF₃ | 4-OCH₃ | $-H$ | 2 |
| 24 | $-SC_2H_5$ | $-H$ | $-CH_3$ | 6-Cl | 4-OCH₃ | $-H$ | 2 |
| 25 | $-SCH_3$ | $-H$ | $-CH_3$ | 6-CF₃ | 4-OCH₃ | $-H$ | 3 |
| 26 | $-N=N=N$ | $-H$ | $-CH_3$ | 7-CF₃ | 4-OCH₃ | $-H$ | 2 |
| 27 | $-NH-C(O)CH_3$ | $-H$ | $-CH_3$ | 7-CF₃ | 4-OCH₃ | $-H$ | 3 |
| 28 | $-NH_2$ | $-H$ | $-CH_3$ | 6-CF₃ | 4-OCH₃ | $-H$ | 2 |
| 29 | $-NH-C_6H_5$ | $-H$ | $-CH_3$ | 7-CF₃ | 4-OCH₃ | $-H$ | 3 |
| 30 | $-SCH_3$ | $-H$ | $-CH_3$ | 7-Cl | 4-OCH₃ | $-H$ | 2 |

What is claimed is:

1. A compound having the formula

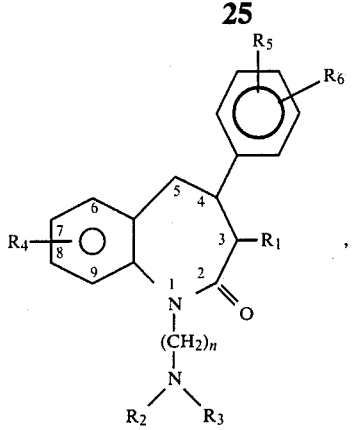

including pharamceutically acceptable salts thereof, wherein

R₁ is

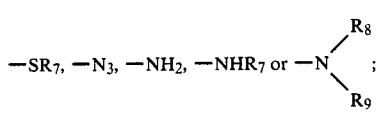

R₂ and R₃ are each independently hydrogen, alkyl, cylcloalkyl or arylalkyl, or R₂ and R₃ together with the nitrogen atom to which they are attached are pyrrolidinyl, piperidinyl, or morpholinyl;

R₄, R₅ and R₆ are each independently hydrogen, halogen, alkyl, alkoxy, aryloxy, arylalkoxy, diarylalkoxy, arylalkyl, cyano, hydroxy, alkanoyloxy,

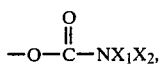

fluoro substittuted alkoxy, fluoro substituted alkyl, (cycloalkyl)alkoxy,

—NO₂, —NX₃X₄, —S(O)ₘalkyl, —S(O)ₘaryl,

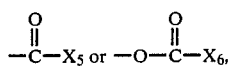

and R₅ and R₆ can be present in the ortho, meta or para positions;

R₇ is carboxylic acid acyl, alkyl, aryl, or arylalkyl;

R₈ and R₉ are each independently hydrogen, alkyl, aryl, cycloalkyl or arylalkyl;

n is 2 or 3;

m is 0, 1 or 2;

X₁ and X₂ are each independently hydrogen, alkyl, aryl or heteroaryl, or X₁ and X₂ together with the nitrogen atom to which they are attached are pyrrolidinyl, piperidinyl or morpholinyl;

X₃ and X₄ are each independently hydrogen, alkyl, alkanoyl, arylcarbonyl, heteroarylcarbonyl, or

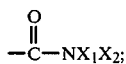

X₅ is hydroxy, alkoxy, aryloxy, amino, alkylamino or dialkylamino; and

X₆ is akyl, alkoxy or aryloxy; with the proviso that if R₄ is a 7-alkyl group, it must have a tertiary carbon atom bonded to the ring; and further wherein the terms "alkyl" and "alkoxy", by themselves or as part of another group, refer to both straight and branched chain groups having 1 to 10 carbon atoms;

the term "alkenyl", by itself or as part of another group, refers to both straight and branched chain groups having 2 to 10 carbon atoms;

the term "aryl", by itself or as part of another group, refers to phenyl and phenyl substituted with 1, 2 or 3 groups independently selected from amino, alkylamino, dialkylamino, nitro, halogen, hydroxyl, trifluoromethyl, alkyl of 1 to 4 carbon atoms, alkoxy of 1 to 4 carbon atoms, alkanoyloxy, carbamoyl, or carboxyl;

the term "alkanoyl", by itself or as part of another group, refers to groups having the formula alkyl

having 2 to 11 carbon atoms;

the term "heteroaryl" refers to pyridinyl, pyrrolyl imidazolyl, furyl, thienyl and thiazolyl;

the term "cycloalkyl" refers to groups haing 3, 4, 5, 6 or 7 carbon atoms; and, the terms "fluoro substituted alkyl" and "fluoro substituted alkoxy", by themselves or as part of another group, refer to said alkyl and said alkoxy groups in which one or more hydrogens have been replaced by fluorine atoms.

2. A compound of claim 1 wherein
R₁ is —S—CH₃, —S—acetyl, and —N₃;
R₂ and R₃ are each methyl or R₂ is hydrogen and R₃ is methyl;
R₄ is 7-trifluorometyl or 6-trifluoromethyl;
R₅ is 4-methoxy; and
R₆ is hydrogen.

3. The d-cis enantimer of a compound of claim 1.

4. The compound of claim 1 being the trans-isomer wherein R₁ is —SCH₃, R₂ and R₃ are each methyl, R₄ is 7-trifluoromethyl, R₅ is 4-methoxy and R₆ is hydrogen.

5. The compound of claim 1 being the cis-isomer wherein R₁ is —SCH₃, R₂ and R₃ are each methyl, R₄ is 7-trifluoromethyl, R₅ is 4-methoxy and R₆ is hydrogen.

6. The compound of claim 1 being the cis-isomer wherein R₁ is —S—acetyl, R₂ and R₃ are each methyl, R₄ is 7-trifluoromethyl, R₅ is 4-methoxy and R₆ is hydrogen.

7. The compound of claim 1 being the cis-isomer wherein R₁ is —N₃, R₂ and R₃ are each methyl, R₄ is 7-chloro, R₅ is 4-methoxy and R₆ is hydrogen.

8. The compound of claim 1 being the cis-isomer wherein R₁ is —N₃, R₂ and R₃ are each methyl, R₄ is 7-trifluoromethyl, R₅ is 4-methoxy and R₆ is hydrogen.

9. The compound of claim 1 being the cis-isomer wherein R₁ is —NH—acetyl, R₂ and R₃ are each methyl, R₄ is 7-trifluoromethyl, R₅ is 4-methoxy and R₅ is hydrogen.

10. The compound of claim 1 having the name (trans)-1-[2-(dimethylamino)ethyl]-1,3,4,5-tetrahydro-4-(4-methoxyphenyl)-3-(methylthio)-7-(trifluoromethyl)-2H-1-benzazepin-2-one, monohydrochloride.

11. The compound of claim 1 having the name (cis)-1-[2-(dimethylamino)ethyl]-1,3,4,5-tetrahydro-4-(4- methoxyphenyl)-3-(methylthio)-7-trifluoromethyl)-2H-1-benzazepin-2-one, monohydrochloride.

12. The compound of claim 1 having the name (cis)-3-(acetylthio)-1-[2-(dimethylamino)ethyl]-1,3,4,5-tetrahydro-4-(4-methoxyphenyl)-7-(trifluoromethyl)-2H-1-benzazepin-2-one, monohydrochloride.

13. The compound of claim 1 having the name (cis)-3-azido-7-chloro-1-[2-(dimethylamino)ethyl]-1,3,4,5-tetrahydro-4-(4-methoxyphenyl)-2H-1-benzazepin-2-one, monohydrochloride.

14. The compound of claim 1 having the name (cis)-3-azido-1-[2-(dimethylamino)ethyl]-1,3,4,5-tetrahydro-4-(4-methoxyphenyl)-7-(trifluoromethyl)-2H-1-benzazepin-2-one, monohydrochloride.

15. The compound of claim 1 having the name (cis)-3-(acetylamino)-1-[2-(dimethylamino)ethyl]-1,3,4,5-tetrahydro-4-(4-methoxyphenyl)-7-(trifluoromethyl)-2H-1-benzazepin-2-one, monohydrochloride.

16. A composition useful in reducing blood pressure in a mammal comprising a pharmaceutically acceptable carrier and an anti-hypertensively effective amount of a compound or pharmaceutically acceptable salt thereof of the formula

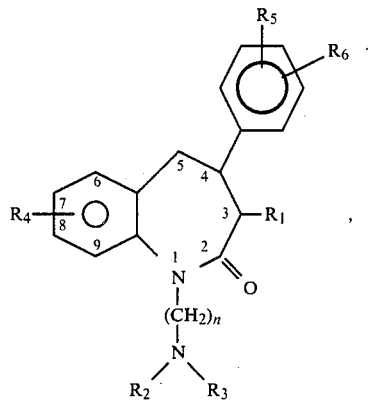

wherein $R_1$, $R_2$, $R_3$, $R_4$, $R_5$, $R_6$ and n are as defined in claim 1.

17. The method of reducing blood pressure in a mammal comprising administering an effective amount of the composition of claim 16.

18. 7-(Trifluorometyl)-1,3,4,5-tetrahydro-3-(p-toluenesulfonyloxy)-4-(4-methoxyphenyl)-2H-1-benzazepin-2-one.

19. (trans)-7-Chloro1,3,4,5-tetrahydro-3-(p-toluenesulfonyloxy)-4-(4-methoxyphenyl)-2H-1-benzazepin-2-one.

20. (trans)-2-(Trifluoromethyl)-1,3,4,5-tetrahydro-3-(p-toluenesulfonyloxy)-4-(4-methoxyphenyl)-2H-1-benzazepin-2-one.

* * * * *